United States Patent [19]

Yamato et al.

[11] 4,451,637
[45] May 29, 1984

[54] EPOXY RESIN COMPOSITION

[75] Inventors: Motoyuki Yamato, Oiso; Tadao Natsuume, Yokosuka, both of Japan

[73] Assignee: Nippon Zeon Co., Ltd., Tokyo, Japan

[21] Appl. No.: 463,024

[22] Filed: Feb. 1, 1983

[30] Foreign Application Priority Data

Feb. 8, 1982 [JP] Japan .................................. 57-18372

[51] Int. Cl.³ .............................................. C08G 59/42
[52] U.S. Cl. .................................... 528/115; 528/112; 528/361; 528/365; 252/182
[58] Field of Search ............... 528/112, 115, 365, 361; 252/182

[56] References Cited

U.S. PATENT DOCUMENTS

| | | | |
|---|---|---|---|
| 3,373,171 | 3/1968 | Lucas et al. | 528/112 X |
| 3,470,132 | 9/1969 | Ernst et al. | |
| 3,600,384 | 8/1971 | Holtz | 528/112 X |
| 3,789,038 | 1/1974 | Curtis et al. | |
| 4,371,688 | 2/1983 | Moore | 528/115 X |

*Primary Examiner*—Earl A. Nielsen
*Attorney, Agent, or Firm*—Sherman & Shalloway

[57] ABSTRACT

A heat-curable epoxy resin composition comprising (A) an epoxy resin and (B) an acid anhydride curing agent liquid at 20° C. composed of, based on acid anhydride equivalents, of 10 to 70% of a tetrabasic acid anhydride represented by the following formula

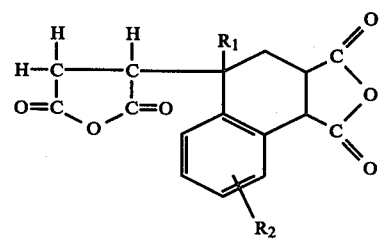

wherein
  $R_1$ represents hydrogen or a methyl group, and
  $R_2$ represents hydrogen or a lower alkyl group, and 30 to 90% of a liquid alicyclic dibasic acid anhydride.

8 Claims, No Drawings

EPOXY RESIN COMPOSITION

This invention relates to a heat-curable epoxy resin composition containing a liquid mixture of a tetrabasic acid anhydride and a dibasic acid anhydride as a curing agent. More specifically, it relates to a heat-curable epoxy resin composition containing a liquid curing agent having excellent storage stability which gives a cured product having excellent heat resistance and mechanical properties.

There have previously been known liquid dibasic acid anhydrides, such as a structural isomeric mixture or a stereoisomeric mixture of methyltetrahydrophthalic anhydride, methylhexahydrophthalic anhydride or 3,6-endomethylenemethyltetrahydrophthalic anhydride, as curing agents for epoxy resins. Because of their excellent handlability and penetrability, these liquid acid anhydride curing agents are widely used in the fields of cast articles, laminated boards, adhesives, etc. However, cured products of epoxy resins obtained with these liquid acid anhydride curing agents have limited heat resistance. For example, a cured product of a bisphenol A-type liquid epoxy resin obtained by curing with methyltetrahydrophthalic anhydride has a heat distortion temperature of 120° C. at the highest.

It is known on the other hand to use tetrabasic acid anhydrides such as benzophenonetetracarboxylic anhydride, pyromellitic anhydride, cyclopentanetetracarboxylic anhydride, butanetetracarboxylic anhydride, or compounds of the formula

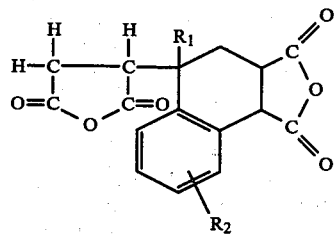

wherein
$R_1$ represents hydrogen or a methyl group, and
$R_2$ represents hydrogen or a lower alkyl group,
as curing agents for epoxy resins in order to increase the heat distortion temperature of cured epoxy resin products (for example, Japanese Patent Publication No. 30028/1979). These tetrabasic acid dianhydrides, however, have the serious defect that they have poor handlability because of their generally high melting points, and partial curing of the epoxy resins begins during heat melting and makes it impossible to obtain a uniform cured product.

A method is known for improving the handlability of a certain kind of tetrabasic acid anhydride by mixing it with a dibasic acid anhydride and thereby decreasing its melting point. But since the tetrabasic acid anhydride generally has poor compatibility with a liquid dibasic acid anhydride, a liquid acid anhydride mixture substantially having excellent storage stability cannot be obtained. Furthermore, an epoxy resin cured product obtained by using the tetrabasic acid anhydride has a high crosslinking density, and therefore has the serious defect that it generally becomes a cured product of brittle nature.

It is an object of this invention to provide a liquid curing agent for epoxy resins which is composed of a tetrabasic acid anhydride and a dibasic acid anhydride and has excellent compatibility, handlability and storage stability.

Another object of this invention is to provide an epoxy resin composition which contains such a curing agent and gives a cured product having excellent heat resistance and mechanical properties.

According to this invention, these objects are achieved by an acid anhydride curing agent which is liquid at 20° C. and is composed of, based on acid anhydride equivalents, 10 to 70% of a tetrabasic acid anhydride represented by formula [I] and 30 to 90% of a liquid alicyclic dibasic acid anhydride; and a heat-curable epoxy resin composition comprising an epoxy resin and the aforesaid curing agent.

The curing agent in accordance with this invention is composed of the tetrabasic acid anhydride of general formula (I) and the liquid alicyclic dibasic acid anhydride. The tetrabasic acid anhydride as a first component is an addition product of 1 mole of a styrene-type monomer such as styrene, α-methylstyrene, vinyltoluene, isopropenyltoluene or p-tertiary butylstyrene and 2 moles of maleic anhydride, which can be easily obtained in a known manner by reacting the styrene-type monomer with maleic anhydride in the presence or absence of a polymerization inhibitor or an inert solvent (see, for example, Japanese Patent Publications Nos. 2986/1969 and 30026/1979). An adduct of α-methylstyrene and maleic anhydride has excellent resistance to moisture absorption, and is especially preferred.

The dibasic acid anhydride as a second component is an alicyclic dibasic acid anhydride which is liquid at 20° C. Specific examples of the second component include a structural isomeric mixture of methyl-Δ⁴-tetrahydrophthalic anhydride, a stereoisomeric mixture of methyl-Δ⁴-tetrahydrophthalic anhydride, methylhexahydrophthalic anhydride, and 3,6-endomethylenemethyltetrahydrophthalic anhydride. The stereoisomeric mixture of methyl-Δ⁴-tetrahydrophthalic anhydride is especially preferred from the standpoint of storage stability. Solid dibasic acid anhydrides such as tetrahydrophthalic anhydride and hexahydrophthalic anhydride are also included within the scope of this invention if a eutectic mixture of such a solid dibasic acid anhydride and the tetrabasic acid anhydride is liquid at 20° C.

In the present invention, a mixture of 10 to 70%, preferably 15 to 65%, of the first component and 30 to 90%, preferably 35 to 85%, of the second component, based on acid anhydride equivalents is used as a curing agent. If the proportion of the first component exceeds 70%, a mixture being liquid at 20° C. cannot be obtained. If it is less than 10%, the effect of improving the heat resistance of the resulting cured product is not sufficient.

The epoxy resin used in this invention contains more than 1, preferably at least 1.5, epoxy groups per molecule. Specific examples of the epoxy resin are glycidyl ether-type epoxy resins synthesized from bisphenol A and epihalohydrins; glycidyl ester-type epoxy resins synthesized from phthalic acid and eiphalohydrins; alicyclic epoxy resins obtained by epoxidizing alicyclic dienes such as cyclopentadiene or cyclohexadiene; epoxidization products of unsaturated polymers such as polybutadiene and polyisoprene; and polymers or copolymers of unsaturated monoepoxides such as glycidyl methacrylate or allyl glycidyl ether. These are merely illustrative, and, for example, it is possible to use various polyhydric phenols instead of bisphenol A, or to use other polybasic acids instead of phthalic acid.

The mixing ratio of the acid anhydride-type curing agent in this invention is such that there are 0.5 to 1.5, preferably 0.6 to 1.2, acid anhydride groups for each epoxy group of the epoxy resin. If this mixing ratio exceeds or falls below the specified limit, the heat distortion temperature of the resulting cured product tends to decrease.

To cure the composition of this invention, it is treated in accordance with a conventional method. For example, a cured product of the composition can be obtained by heating it at a temperature of 50° to 250° C., preferably 100° to 200° C. A reaction promoter such as a tertiary amine, a phenol or an imidazole may be used in the curing process.

The epoxy resin composition of this invention is used mainly in the fields of electrical insulating materials, structural materials and adhesives. Accordingly, as required, the epoxy resin composition of this invention may include reactive diluents, plasticizers, inorganic fillers (e.g., talc, gypsum, alumina or asbestos), pigments, fire retardants, mold releasing agents, defoamers, etc.

The following examples illustrate the present invention more specifically. All parts and percentages in these examples are by weight.

REFERENTIAL EXAMPLE 1

A separable flask equipped with a stirrer was charged with 196 parts (2 moles) of maleic anhydride, 300 parts of toluene and 10 parts of phenothiazine. The flask was heated to 60° C. in an atmosphere of nitrogen to dissolve these compounds uniformly. Then, 118 parts (1 mole) of α-methylstyrene was added over the course of 1 hour. The mixture was heated to 90° C., and reacted at this temperature for 3 hours in an atmosphere of nitrogen. The precipitated product was separated by filtration, and recrystallized from methyl ethyl ketone to give 260 parts of a white solid product.

The properties of the product were measured, and it was found to have a molecular weight of 314, an acid anhydride equivalent of 157 and a melting point of 197° C. Analysis of the structure of the product of $C^{13}$-NMR led to the determination that this product is a tetrabasic acid anhydride of formula (I) in which $R_1$ is a methyl group and $R_2$ is hydrogen (to be referred to as AMS-MAH).

REFERENTIAL EXAMPLE 2

Tetrabasic acids were prepared in the same way as in Referential Example 1 except that 104 parts (1 mole) of styrene and 118 parts (1 mole) of vinyltoluene were respectively used instead of α-methylstyrene. The properties and structures of these tetrabasic acids are shown in Table 1.

TABLE 1

| Starting materials | Product | | | | |
|---|---|---|---|---|---|
| | Molecular weight | Acid anhydride equivalent | Melting point (°C.) | Chemical structure (in formula [I]) | Abbreviated name |
| Styrene | 300 | 150 | 203 | $R_1$ and $R_2$ = hydrogen | ST-MAH |
| Vinyltoluene | 314 | 157 | 190 | $R_1$ = hydrogen, $R_2$ = methyl | VT-MAH |

EXAMPLE 1

A separable flask equipped with a stirrer was charged with each of the tetrabasic acid anhydrides and each of the dibasic acid anhydrides indicated in Table 2 in the proportions indicated in Table 2. They were melted at 220° C., and then cooled. The viscosity of the resulting mixture was measured at 20° C., and then it was stored at 20° C. The number of days which elapsed until crystals precipitated was determined. The results are shown in Table 2.

The results given in Table 2 demonstrate that the curing agents in accordance with this invention maintain a stable liquid state at 20° C. for a longer period of time than those containing other tetrabasic acid anhydrides.

TABLE 2

| | Run No. | | | | | | | | | | |
|---|---|---|---|---|---|---|---|---|---|---|---|
| | Comparison | Invention | | | | | | | Comparison | | |
| | 1-1 | 1-2 | 1-3 | 1-4 | 1-5 | 1-6 | 1-7 | 1-8 | 1-9 | 1-10 | 1-11 |
| First component (tetrabasic acid anhydride) (parts) | | | | | | | | | | | |
| AMS-MAH | 100 | 100 | 100 | 100 | 100 | — | — | — | — | — | — |
| ST-MAH | — | — | — | — | — | 100 | 100 | — | — | — | — |
| VT-MAH | — | — | — | — | — | — | — | 100 | — | — | — |
| Benzophenonetetracarboxylic dianhydride | — | — | — | — | — | — | — | — | 100 | — | — |
| Pyromellitic dianhydride | — | — | — | — | — | — | — | — | — | 100 | — |
| Cyclopentanetetracarboxylic dianhydride | — | — | — | — | — | — | — | — | — | — | 100 |
| Second component (dibasic acid anhydride) (parts) | | | | | | | | | | | |
| Quinhard-200 (*1) | 26.4 | 317.2 | 105.7 | — | — | 26.4 | — | — | 103.1 | — | — |
| HN-2200R (*2) | — | — | — | 105.7 | — | — | 110.7 | — | — | 152.3 | — |
| Epiclon-B-650 (*3) | — | — | — | — | 107.0 | — | — | 107.0 | — | — | 106.0 |
| 1st component/2nd component (acid anhydride equivalent ratio) | 80/20 | 25/75 | 50/50 | 50/50 | 50/50 | 25/75 | 50/50 | 50/50 | 50/50 | 50/50 | 50/50 |
| Viscosity of the mixture (cps/20° C.) | 100,000< | 300 | 14,000 | 15,000 | 16,000 | 320 | 16,000 | 13,500 | (*4) | (*4) | (*4) |
| Storage stability (number of days elapsed until crystals precipitated | 3 | 7< | 7< | 7< | 7< | 7< | 7< | 7< | 1> | 1> | 1> |

TABLE 2-continued

| | Run No. | | | | | | | | | | |
|---|---|---|---|---|---|---|---|---|---|---|---|
| | Comparison | Invention | | | | | | | Comparison | | |
| | 1-1 | 1-2 | 1-3 | 1-4 | 1-5 | 1-6 | 1-7 | 1-8 | 1-9 | 1-10 | 1-11 |
| during storage at 20° C.) | | | | | | | | | | | |

(*1): tradename for a stereoisomeric mixture of methyltetrahydrophthalic anhydride produced by Nippon Zeon Co., Ltd.
(*2): tradename for a structural isomeric mixture of methyltetrahydrophthalic anhydride produced by Hitach Chemical Co., Ltd.
(*3): tradename for 3-methylhexahydrophthalic anhydride produced by Dainippon Ink & Chemicals Co., Ltd.
(*4): The viscosity could not be measured because crystals rapidly precipitated when the mixture was cooled to the temperature at which the viscosity was to be measured.

EXAMPLE 2

A liquid epoxy resin (Epikote 828, a tradename for a product of Shell Chemical Co.; epoxy equivalent 190), an acid anhydride curing agent and a curing promoter were mixed in the proportions shown in Table 3. The mixture was poured into a mold, and heat-cured at 100° C. for 5 hours and then at 165° C. for 3 hours. In RUN No. 2-4, the following procedure was taken because AMS-MAH has a high melting point. The liquid epoxy resin and AMS-MAH were first mixed at 180° C. for 30 minutes. The mixture was cooled to 130° C., and then mixed with benzyldimethylamine. The mixture was cured at 165° C. for 5 hours, and then at 200° C. for 3 hours.

The results given in Table 3 demonstrate that the compositions of this invention have improved heat resistance over the composition containing only the liquid dibasic acid anhydride as a curing agent, and give cured products which are mechanically tough and have greatly improved flexural properties, although having slightly decreased heat resistance, over the composition containing A only AMS-MAH as a curing agent.

TABLE 3

| | Run No. | | | |
|---|---|---|---|---|
| | Control | Invention | | Control |
| | 2-1 | 2-2 | 2-3 | 2-4 |
| Epikote 828 (Parts) | 100 | 100 | 100 | 100 |
| AMS-MAH | — | 18.6 | 37.2 | 74.4 |
| Quinhard-200 (*1) | 78.6 | 59.0 | 39.3 | — |
| Benzyldimethylamine | 0.2 | 0.2 | 0.2 | 0.2 |
| AMS-MAH/Quinhard-200 (acid anhydride equivalent ratio) | 0/100 | 25/75 | 50/50 | 100/0 |
| Acid anhydride groups/ epoxy groups (equivalent ratio) | 90/100 | 90/100 | 90/100 | 90/100 |
| Properties of the cured product | | | | |
| Heat distortion temperature (°C.) | 119 | 142 | 165 | 210 |
| Flexural strength (25° C., kg/mm²) | 13.1 | 14.5 | 13.0 | 7.5 |
| Flexural modulus (25° C., kg/mm²) | 315 | 364 | 374 | 320 |

(*1): Same as the footnote to Table 2.

EXAMPLE 3

A cured product was obtained in the same way as in Example 2 except that Quinhard-200 was replaced by another alicyclic dibasic acid anhydride as shown in Table 4. The properties of the cured product were measured, and are shown in Table 4. The results show that as in Example 2, the cured products in accordance with this invention have improved heat resistance and flexural properties over those of the controls.

TABLE 4

| | Run No. | | | |
|---|---|---|---|---|
| | Control | | Invention | |
| | 1 | 2 | 3 | 4 |
| Epikote-828 (Parts) | 100 | 100 | 100 | 100 |
| AMS-MAH | — | — | 37.2 | 37.2 |
| HN-2200R (*2) | 78.6 | — | 39.3 | — |
| Epiclon B-650 (*3) | — | 79.6 | — | 39.8 |
| Benzyldimethylamine | 0.2 | 0.2 | 0.2 | 0.2 |
| AMS-MAH/dibasic acid anhydride (acid anhydride equivalent ratio) | 0/100 | 0/100 | 50/50 | 50/50 |
| Acid anhydride groups/epoxy groups (equivalent ratio) | 90/100 | 90/100 | 90/100 | 90/100 |
| Properties of the cured product | | | | |
| Heat distortion temperature (°C.) | 117 | 131 | 140 | 173 |
| Flexural strength (25° C., kg/mm²) | 13.0 | 13.2 | 13.5 | 13.4 |
| Flexural modulus (25° C., kg/mm²) | 313 | 302 | 370 | 365 |

(*2) and (*3): Same as the footnote to Table 2.

EXAMPLE 4

Run No. 2-3 of Example 2 was repeated except that VT-MAH was used instead of AMS-MAH. Nearly the same results as in the case of using AMS-MAH were obtained.

What is claimed is:

1. A heat-curable epoxy resin composition comprising (A) an epoxy resin and (B) an acid anhydride curing agent liquid at 20° C. composed of, based on acid anhydride equivalents, of 10 to 70% of a tetrabasic acid anhydride represented by the following formula

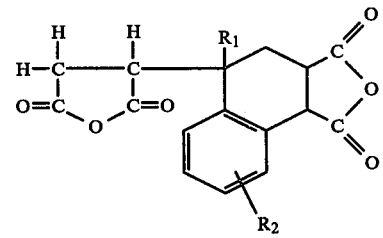

wherein
$R_1$ represents hydrogen or a methyl group, and
$R_2$ represents hydrogen or a lower alkyl group,
and 30 to 90% of a liquid alicyclic dibasic acid anhydride.

2. The composition of claim 1 wherein the content of the acid anhydride curing agent (B) is such that there are 0.5 to 1.5 acid anhydride groups for each epoxy group of the epoxy resin (A).

3. The composition of claim 1 wherein the tetrabasic acid anhydride is an addition product between 1 mole of styrene, α-methylstyrene, vinyltoluene, isopropenyltoluene or p-tertiary butylstyrene and 2 moles of maleic anhydride.

4. The composition of claim 1 wherein the tetrabasic acid anhydride is an addition product between 1 mole of α-methylstyrene and 2 moles of maleic anhydride.

5. The composition of claim 1 wherein the dibasic acid anhydride is a structural isomeric mixture of methyl-$\Delta^4$-tetrahydrophthalic anhydride, a stereoisomeric mixture of methyl-$\Delta^4$-tetrahydrophthalic anhydride, methylhexahydrophthalic anhydride, or 3,6-endomethylenemethyltetrahydrophthalic anhydride.

6. The composition of claim 1 wherein the dibasic acid anhydride is a stereoisomeric mixture of methyl-$\Delta^4$-tetrahydrophthalic anhydride.

7. A cured resin product produced by heat-curing the composition of any one of the preceding claims.

8. A curing agent for epoxy resins, said curing agent being liquid at 20° C. and being composed of, based on acid anhydride equivalents, 10 to 70% of a tetrabasic acid anhydride represented by the following formula

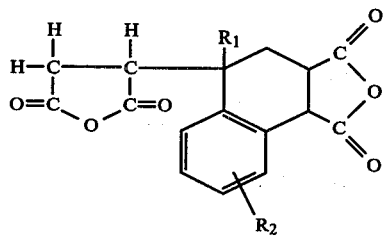

wherein
  $R_1$ represents hydrogen or a methyl group, and
  $R_2$ is hydrogen or a lower alkyl group,
and 30 to 90% of a liquid alicyclic dibasic acid anhydride.

* * * * *